United States Patent
Nemetz et al.

[19]

[11] Patent Number: 6,149,430
[45] Date of Patent: Nov. 21, 2000

[54] INTEGRALLY MOLDED DENTAL APPLIANCE AND PROCESS FOR ITS MANUFACTURE

[75] Inventors: Annette M. Nemetz, Sherwood; Joshua K. Hoyt, Portland; Bruno Rudolf Rux, Beaverton, all of Oreg.

[73] Assignee: Ora Innovations, Inc., Portland, Oreg.

[21] Appl. No.: 09/027,046

[22] Filed: Feb. 20, 1998

[51] Int. Cl.[7] .................................................. A61C 1/08
[52] U.S. Cl. .......................... 433/132; 433/125; 433/126
[58] Field of Search .................................. 433/125, 126, 433/127, 128, 129, 132

[56] References Cited

U.S. PATENT DOCUMENTS

| | | |
|---|---|---|
| Re. 29,687 | 7/1978 | Sertich . |
| Re. 31,965 | 8/1985 | Kerfoot, Jr. . |
| D. 214,053 | 5/1969 | Grossman . |
| D. 239,390 | 3/1976 | Webb . |
| D. 241,550 | 9/1976 | Morin . |
| D. 251,304 | 3/1979 | Leonard . |
| D. 263,877 | 4/1982 | Rodszus et al. . |
| D. 269,122 | 5/1983 | Seeley . |
| D. 305,935 | 2/1990 | Straihammer et al. . |
| D. 356,866 | 3/1995 | Meller . |
| 3,120,706 | 2/1964 | Turchi et al. . |
| 3,631,597 | 1/1972 | Lieb et al. . |
| 3,893,242 | 7/1975 | Lieb et al. . |
| 3,947,966 | 4/1976 | Lieb et al. . |
| 3,955,284 | 5/1976 | Balson . |
| 4,015,335 | 4/1977 | Nash et al. . |
| 4,015,489 | 4/1977 | Lieb et al. . |
| 4,017,974 | 4/1977 | Sotman et al. . |
| 4,020,556 | 5/1977 | Sotman . |
| 4,117,597 | 10/1978 | Trist et al. . |
| 4,171,572 | 10/1979 | Nash . |

(List continued on next page.)

FOREIGN PATENT DOCUMENTS 2 209 284   5/1989   United Kingdom .

OTHER PUBLICATIONS

Press Release entitled *CoreTech to Market "Lost–Core" Molding Technology Services and Equipment*, CoreTech Associates, Inc., May 29, 1996.

Services brochure entitled *Metal Core Technology (MCT) Engineering, Prototyping, Equipment, Tooling and Management Services*, CoreTech Associates, Inc. Nov., 1995.

MDD News news article entitled *Freudenberg to Use Electrovert–MDD Cell for GM's Northstar Manifold* [publication date unknown].

Miscellaneous advertising entitled *Disposable Handpiece protects against disease transmission*, [publication date uknown].

Oralsafe disposable handpiece brochure.

(List continued on next page.)

*Primary Examiner*—Nicholas D. Lucchesi
*Attorney, Agent, or Firm*—Marger Johnson & McCollom

[57] ABSTRACT

The invented dental apparatus and method for its manufacture involves an integrally molded, polymeric, unitary, hand piece having fluid conduits formed therein during the molding process for conducting fluid, e.g. air, under pressure from a proximal end having an industry standard couple to a distal end including an integrally molded head piece for housing a rotary, preferably canister-type turbine to which a dental bur may be removably secured. Preferably, an integrally molded venturi chamber fluid-interconnects a pressurized one of the conduits and an inlet to the turbine's impeller and an outlet of the turbine's impeller is fluid-connected at an outlet of the canister to an exhaust one of the conduits. Optionally, one or more chip-air source conduits and a light valve may extend within the elongate interior of the hand piece to provide intra-oral, in-process cleaning, cooling and lighting functions. Preferably, the hand piece is injection molded via a lost-material, e.g. a lost-metal, process similar to investment casting. The invented hand piece, in its preferred embodiment, is autoclavable and disposable.

21 Claims, 2 Drawing Sheets

U.S. PATENT DOCUMENTS

| | | |
|---|---|---|
| 4,203,221 | 5/1980 | Knopp et al. . |
| 4,249,896 | 2/1981 | Kerfoot, Jr. . |
| 4,283,174 | 8/1981 | Sertich . |
| 4,283,175 | 8/1981 | Nash . |
| 4,315,742 | 2/1982 | Nash et al. . |
| 4,330,282 | 5/1982 | Nash . |
| 4,375,964 | 3/1983 | Kropp et al. . |
| 4,470,812 | 9/1984 | Martens et al. . |
| 4,614,498 | 9/1986 | Vaccaro . |
| 4,648,838 | 3/1987 | Schlachter . |
| 4,669,982 | 6/1987 | Fleer . |
| 4,681,540 | 7/1987 | Landgraf et al. . |
| 4,711,630 | 12/1987 | Durr . |
| 4,842,516 | 6/1989 | Chosser . |
| 4,921,424 | 5/1990 | Kimura . |
| 4,941,828 | 7/1990 | Kimura . |
| 4,973,247 | 11/1990 | Varnes et al. . |
| 4,975,058 | 12/1990 | Woodward . |
| 4,978,297 | 12/1990 | Vlock . |
| 4,983,121 | 1/1991 | Straihammer et al. . |
| 5,039,304 | 8/1991 | Heil . |
| 5,088,924 | 2/1992 | Woodward . |
| 5,120,220 | 6/1992 | Butler . |
| 5,139,422 | 8/1992 | Straihammer et al. . |
| 5,145,370 | 9/1992 | Woodward . |
| 5,156,547 | 10/1992 | Bailey . |
| 5,160,263 | 11/1992 | Meller et al. . |
| 5,252,067 | 10/1993 | Kakimoto . |
| 5,308,242 | 5/1994 | McLaughlin et al. . |
| 5,336,089 | 8/1994 | Sakurai . |
| 5,374,189 | 12/1994 | Mendoza . |
| 5,507,642 | 4/1996 | Wohlgemuth ............................ 433/132 |
| 5,538,425 | 7/1996 | Reeves et al. . |
| 5,667,383 | 9/1997 | Mendoza et al. . |
| 5,772,435 | 6/1998 | Dorman ............................... 433/132 X |
| 5,772,436 | 6/1998 | Matsui et al. ........................ 433/132 X |
| 5,797,743 | 8/1998 | Bailey ................................. 433/132 X |
| 5,800,172 | 9/1998 | Goldenberg ............................ 433/132 |

OTHER PUBLICATIONS

Article entitled *Local Dentist Leading Way in Field* believed to have been published in a Carlsbad, California newspaper at least as early as Jul. 2, 1992.

Miscellaneous Advertising, *The "Disposable" Dental Handpiece*, Oralsafe™, [publication date unknown].

Brochure entitled *Metal Core Technology & LMD 2000 Equipment*, CoreTech Associates, Inc., [publication date unknown].

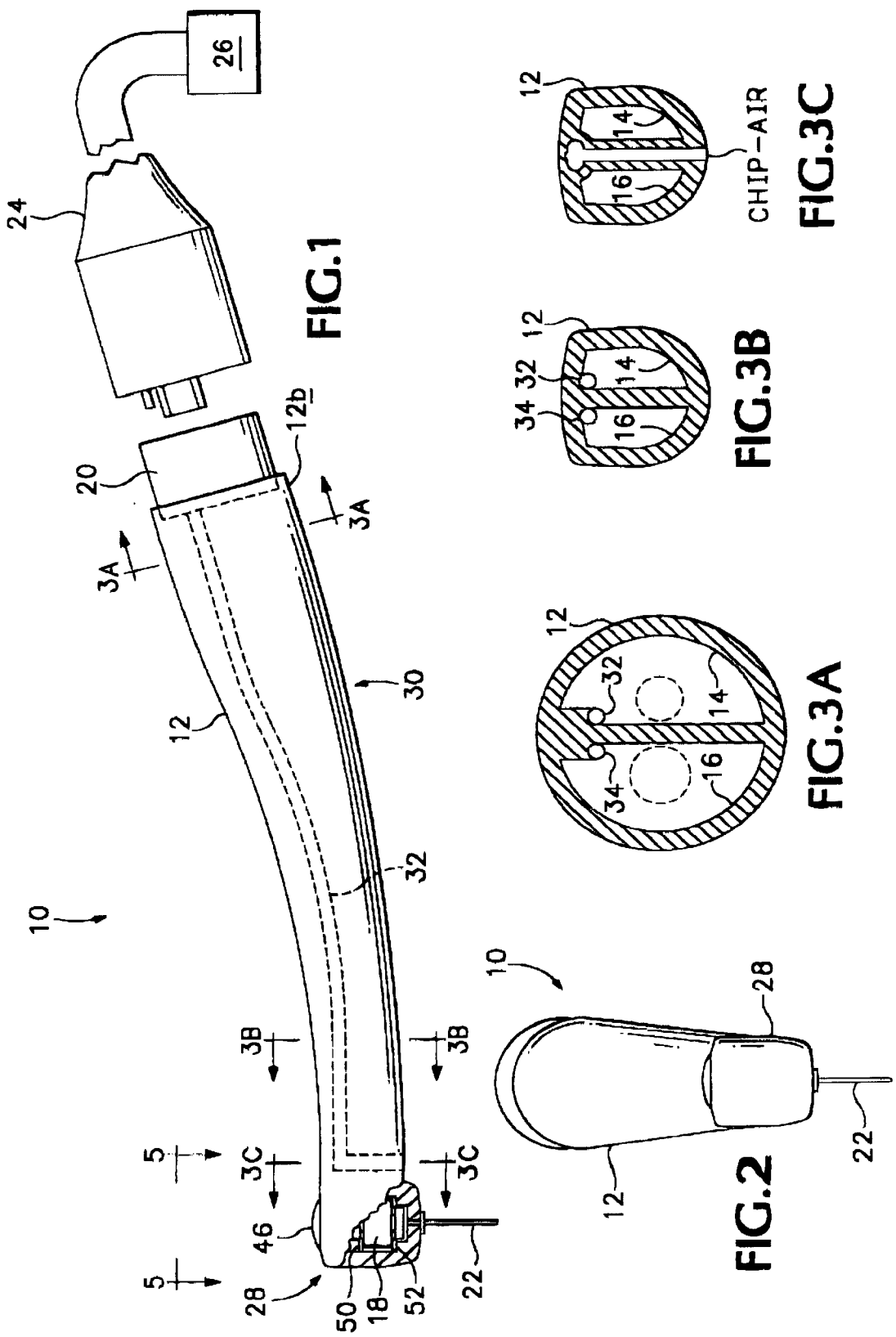

INTEGRALLY MOLDED DENTAL APPLIANCE AND PROCESS FOR ITS MANUFACTURE

TECHNICAL FIELD

The present invention relates generally to dental appliances such as hand-held tools used intra-orally with dental patients. More particularly, it concerns, rotary tools used for drilling, cleaning and polishing teeth by pneumatic and/or hydraulic, turbine-driven mechanisms.

BACKGROUND ART

There have been prior attempts to improve the manufacturability of dental hand pieces. For example, Great Britain publication GB 2 209 284 A to Hiroshi Kimura describes a dental hand piece made of synthetic resin that is integrally molded as one piece. A detachable head piece snap-fits onto the distal end of the hand piece, which is hollow and thin-walled to accommodate the extension therethrough of two fluid conduits in the form of tubes described as being captured during the resin casting process (see page 7, first partial paragraph, last sentence). The reference does not explain precisely how the hand piece is molded, and there is no suggestion of investment casting, and the insertion of tubes in the interior instead the formation of conduits therein is contrary to such a suggestion.

U.S. Pat. No. 4,842,516 to Choisser teaches a disposable prophylactic hand tool having a right-angled head for cleaning, polishing etc. It is preferably made of plastic that presumably is not autoclavable (see column 1, lines 25 through 39 re prior art hygiene problems). A plastic turbine drive mechanism is also described as disposable. A bearing between the plastic endwall and the turbine is said to reduce frictional wear. (See column 3, lines 51 through 59.)

U.S. Pat. No. 5,308,242 to McLaughlin, et al. teaches a disposable hand piece for high-speed drilling, etc. in a two-piece, clamshell arrangement whereby two opposing axial halves are joined along two axial seams (see FIGS. 3A, 3B), but in which the air and/or fluid conduits are integrally molded into either shell half by conventional injection molding (see column 2, lines 39 through 54). The Oralsafe Co. of Temecula, Calif. attempted to make such a disposable, so-called "high-impact" plastic hand piece for use in a high-speed drilling dental application, and, because of the clamshell construction of its hand piece, failed to produce a product that could be repeatably manufactured in such manner as to enable reliable, long-term, high-speed drilling and its attendant fluid pressure and ultra-high-frequency vibration.

U.S. Pat. No. 5,374,189 to Mendoza teaches an integrally formed, preferably plastic, "prophy", i.e. prophylactic, dental hand piece intended for single use and disposal. The reference teaches away from autoclaving as too costly (see column 1, lines 52 through 64).

U.S. Pat. No. 4,648,838 to Schlachter teaches the inclusion in an integrally molded dental hand piece of a light-emitting element axially aligned and directed with the fluid, e.g. air, water, conduits, which assume the form of hoses or thin tubes extending through a large interior hollow of the hand piece (column 3, line 49 through column 4, line 68).

Prior art attempts to manufacture a durable high-speed dental appliance out of injection molded polymeric material has required seams in critical regions that are incapable of withstanding the stresses to which normal use and maintenance put the dental appliance. For example, one prior art approach is the two-piece clamshell arrangement in which essentially mirror-image elongate half-shells are adhered along opposing elongate seams, which seams have been found to fail under the stress of normal use and maintenance. Another prior art approach is the two-piece handle/head configuration in which a seam extends around the hand piece in a plane normal to the hand piece's long axis between separately molded handle and head, which seam also has been found to fail under the stress of normal use and maintenance. Yet another prior art approach is injection or so-called 'blow' molding of a hand piece having a single elongate passage therethrough defined by thin sidewalls wherein various conduits in the form of discrete tubes are used for driving the turbine, thereby greatly increasing component count, cost and attendance interconnection difficulties and reliability problems.

Even the traditional machined-metal dental drills are typically of at least two-piece construction. None of the prior art teaches an auto-clavable, unitary construction for such a dental appliance.

DISCLOSURE OF THE INVENTION

None of the prior art teaches an auto-clavable, low-cost, integrally molded one-piece body structure in which the interior fluid turbine drive media conduits are formed by investment casting, e.g. a lost-material molding process, like the CoreTech™ process available from CoreTech Associates, Inc, of East Greenwich, R.I., or similar process. Thus, the advantages of multi-patient use with intervening autoclaving and ultimate disposal of a high-performance, high-speed dental hand piece are achieved in the invented Ora Innovations™ dental appliance while component count, adhesive or other material additives, sealed fittings, as well as their attendant cost and complexity and their lack of durability and reliability are avoided. Ora Innovations™ is a trademark owned by the assignee of the present invention.

The invented appliance includes an integrally molded, unitary hand piece having fluid conduits formed therein during the molding process for conducting fluid, e.g. air, under pressure from a proximal end having an industry standard couple to a distal end including an integrally molded head piece for housing a rotary, preferably canister-type turbine to which a dental bur may be removably secured. Preferably, a venturi chamber formed between the canister and a pressurized one of the conduits fluid-interconnects the one of the conduits and the turbine's impeller. In turn, the turbine's impeller is fluid-connected at an outlet of the canister to an exhaust one of the conduits. Optionally, one or more chip-air source conduits and a light valve may be provided within the hand piece to provide intra-oral, in-process cleaning, cooling and lighting functions. Preferably, the hand piece is injection molded via a lost-material, e.g. a lost-metal, process similar to investment casting. The invented hand piece, in its preferred embodiment, is autoclavable and disposable.

These and additional objects and advantages of the present invention will be more readily understood after consideration of the drawings and the detailed description of the preferred embodiment which follows.

BRIEF DESCRIPTION OF THE DRAWINGS

FIG. 1 is a front projection of the invented appliance made in accordance with its preferred embodiment.

FIG. 2 is a partly cross-sectional side elevational view of the invented appliance along with a schematic representation of a drive system therefor.

FIGS. 3A, 3B and 3C are cross-sectional views taken along the lines 3A—3A, 3B—3B and 3C—3C, respectively, of FIG. 2 and showing the interior of the invented appliance made in accordance with its preferred embodiment.

Figure 4:
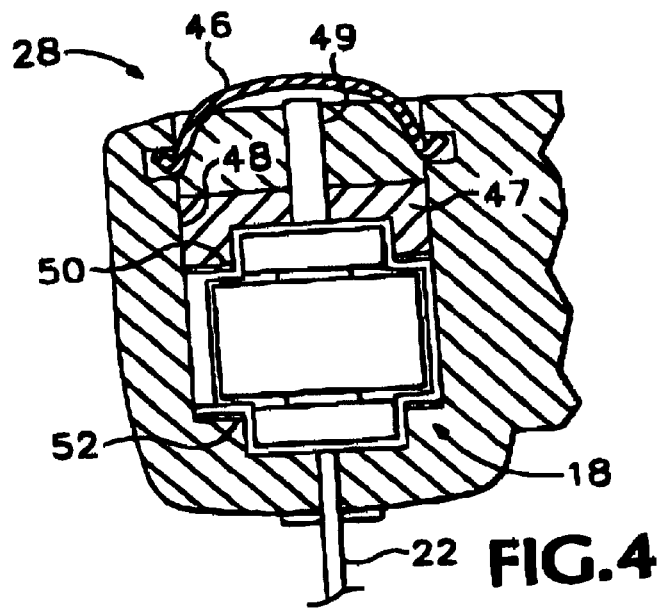
FIG. 4 is an enlarged, fragmentary side elevation corresponding generally to FIGS. 2 and 5B taken generally along the lines 5—5 of the latter, and showing the end cap and push-button detail in the head piece of the invented appliance.

DETAILED DESCRIPTION OF THE PREFERRED EMBODIMENT AND BEST MODE OF CARRYING OUT THE INVENTION

It will be appreciated that typically the drive systems for high-speed rotary dental appliances such as drills are pneumatic, i.e. they use compressed air to drive a rotary impeller of a turbine. Nevertheless, it is believed that hydraulic drive systems wherein the compressed medium is other than air, e.g. water or another fluid, is possible and desirable in some applications. Accordingly, applicants use the term 'fluid' herein to refer most broadly to a liquid-, vapor- or dry-phase medium capable of flowing and thus useful in charging a substantially closed system of conduits for driving a rotary mechanism, e.g. an impeller in a turbine. Those of skill in the art will appreciate then that, although pneumatic systems may presently be preferred, nevertheless air, water, oil or any other fluid medium may be used in such turbine drive systems as the pressurized charging medium, within the spirit and scope of the invention.

FIGS. 1 and 2 are front and side elevational, partly cross-sectional views of the integrally molded hand piece and dental drill, respectively, exemplary of the structure and process made possible by the invention for what is referred to herein as a multiple-use but disposable, low-cost, high-performance dental appliance indicated generally at 10. The invented appliance 10 preferably includes an elongate, obtusely angled body or case 12 made by an injection molding process to provide therethrough one or more, e.g. two, smooth, elongate fluid conduits 14, 16 (refer briefly to FIGS. 3A through 3C) for pneumatic or hydraulic operation of a conventional, preferably sealed canister-style turbine 18 positioned in its distal, head 12a. A metal or plastic threaded insert 20 in a proximal end 12b of case 12 provides for external equipment mating, as better shown in FIG. 2, although it will be appreciated that such may alternatively be integrally molded with case 12. Conventionally, turbine 18 is powered pneumatically or hydraulically via one or more of the conduits and is equipped with one of many interchangeable rotary tools such as fine finishing or polishing heads, or so-called burs, or drill bits, such as bur 22 (preferably captured within a conventional chuck, not shown, located within the central region of a canister turbine assembly).

It will be appreciated by those of skill in the arts that exhaust conduit 16 in cross-sectional area may be approximately the same size as, but preferably is no smaller than, pressurized conduit 14, thereby avoiding back pressure when the conduits are charged and dental appliance 10 is operating. It may also be seen that the cross-sectional surface areas of conduits 14, 16 preferably are dimensioned, in accordance with the invention, to make best use of the lost-material casting process.

The preferred process typically relies on a relatively large cross-sectional surface area because the plugs that define the inner boundaries of the voids used as conduits within the hand piece need a minimum durability effectively to hold the relatively low dimensional tolerances required in the placement, orientation and shape of the resulting conduits. Nevertheless, it will be appreciated that lost-material casting processes are contemplated that relax this cross-sectional surface requirement, and would permit more than two conduits, e.g. a third and fourth conduit used to provide chip-air to the head, to be formed within the circular cross-sectional outline of hand piece 12.

The one or more conduits and optional light valve (not shown) are charged or powered by a cord 24 extending from proximal end 12b of case 12 to a power source 26 shown schematically. Power source 26 will be understood to be of conventional construction and operation, as by a foot pedal that enables the dentist or hygienist to control the speed of rotation, and thus the torque, of the variable speed finisher or polisher. Detailed cross sections A—A through C—C of FIGS. 3A through 3C are believed to be self-explanatory, and will be described only briefly herein by reference to the purpose and character of the various conduits. As described above, pressurized or drive and exhaust or return conduits 14, 16 are generally symmetrically located on either side of a centerline represented physically by a polymer spine of the body of hand piece 12 that separates them. Importantly, they are pressurized fluid-worthy by their material construction such that any leakage that there might be is of no important consequence to the generated torque. The cross-sectional area and shape of conduits 14, 16 are believed to be relatively unimportant to the efficient operation of appliance 10, so long as they are large enough for the chosen fluid, e.g. air, to flow through relatively without obstruction.

Shown in FIGS. 3A and 3B are two relatively tiny, secondary conduits in the form—in accordance with the preferred embodiment of the invention—of two tubes extending the substantial length of what will be referred to herein as a handle 30 for carrying air and water for the chip-air system. Those of skill in the arts will appreciate that these tubes are not in fluid communication with conduits 14, 16 but serve an entirely separate function of supplying chip-air to an outlet in a stream that is directed toward the distal end of the bur where the material removal work is being performed during a dental drilling operation. The chip-air conduits of any suitably autoclavable metal, plastic or rubber, may be insert molded to the interior of molded polymer hand piece 12 and are attached to the chip-air drive system that is a part of power source 26 via a suitable couple provided within the proximal end of appliance 10. (Some drive systems do not provide air, and in such cases typically air is siphoned from the pneumatic drive system e.g. via a cross channel or cross-porting chamber that may be formed in the proximal end of hand piece body 12, e.g. within threaded insert 20 forming a part thereof, extending between one or more of the chip-air conduits and pneumatic drive conduit 14. Within the spirit and scope of the invention, such a modification to the chip-air system described of course may be made.)

It will be appreciated by those of skill that the air and water chip-air conduits discussed in further detail below— instead of being discrete tubes extending within integrally molded conduits 14, 16—may be integrally formed within the interior of hand piece 12 in a manner similar to that of conduits 14, 16. Such an increase in the number of integrally molded conduits within the interior of hand piece 12 will be seen necessarily to either decrease the cross-sectional diameter of each such conduit or to increase the cross-sectional diameter of the hand piece itself. For ergonomic reasons regarding comfort in handling appliance 10 and for technical reasons regarding the lost-material molding process, the preferred embodiment features integrally molded conduits 14, 16 and discrete tube-like conduits shown in FIGS. 3A and 3B and discussed in further detail below. Nevertheless, it will be appreciated that any or all of the needed conduits, including also the optional light valve described above, may be integrally molded within the interior of appliance 10, in accordance with teachings herein and within the spirit and scope of the invention.

FIGS. 3A through 3C illustrate that chip-air conduits 32, 34 preferably do not mix their air and water along the substantial length of hand piece 12. Instead, it has been discovered that mixture preferably occurs near the outlet region on appliance 10 where a coherent stream of the air-water mixture is directed at an angle toward the distal end of bur 22. Thus, FIGS. 1 (dashed lines) and 3C show that the two conduits merge into a single mixing chamber ("CHIP-AIR") which angles downwardly through a single conduit to an exit outlet in a bottom surface of hand piece 12, where it may be directed by suitable means toward the distal end of bur 22. It will be understood that the singular exit conduit for chip-air that is shown in FIG. 3C may be formed as part of the molding process, or may be formed thereafter, as by drilling or machining.

Because of its uniquely integral, injection-molded polymeric construction, appliance 10 can withstand the extreme temperatures associated with autoclaving ($\leq 275°$ F.), which of course is necessary periodically to maintain proper hygiene and safety. Previously, such dental appliances were made of multi-piece stainless steel, at a replacement cost averaging $600, which stainless steel construction withstands autoclaving temperatures but which is too expensive to be disposed of and must be periodically sent from the dentist's office to a lab for maintenance and repair. Importantly, the invented, one-piece polymeric appliance may be used a number of times, with autoclaving between uses, and then may be disposed of and replaced at a substantially lower cost. The invention thus is somewhat analogous to the advent of disposable razors, though of higher quality and reliability.

Preferably, case 12 is manufactured using a proprietary but available so-called metal core technology available from Core Tech Associates, Inc., although it will be understood that any suitable process is contemplated and is within the spirit and scope of the invention. Suitable processes are understood to involve lost-material, e.g. lost-metal, investment casting to produce smooth, burr-free interior conduits in manufactured parts. The present invention utilizes such a lost-material casting method similar to prior art investment casting, e.g. lost-wax, methods to produce a complexly curved and unitary hand piece that is elastic and durable, can withstand autoclaving temperatures and is of sufficiently low cost that it can economically be disposed of after several uses.

It is by the investment casting approach—whereby a void is formed within an otherwise solid casting by introducing into the empty mold one or more plugs representing the desired conduits or other interior features and whereby the plug after casting and curing of the molding compound is removed, as by heating the cast part to a temperature higher than the melting point of the plug(s) but lower than the temperature-withstand capability of the cast part—that complex curvatures and smooth interiors may be constructed both internally and externally in such molded pieces, despite the problematic bend—which also must be traversed by the conduit(s)—that characterizes dental hand tools.

Many of the features of dental appliances are conventional and may be dictated by international standards such as ISO. For example, the diameter and extent of the conduits through the elongate handle portion of case 12 may be dictated, as may be the approximately 15° bend in case 12. The range of angular rotational speeds and torques of the turbine, itself conventional, are also believed to be standard, e.g. $\leq 50,000$ RPM for prophylaxis and fine finishing (so-called low-speed operation) and $\leq 500,000$ RPM for drilling and shaping (so-called high-speed operation), although the canister-style turbine is preferred because it avoids any bearing problems between the dissimilar metal turbine rotor and polymeric case.

As will be seen by reference to FIG. 4, a unique canister configuration that is form fit to smaller diameter roller bearings on either side of the larger diameter turbine's impeller preferably is provided, thereby reducing the size of the hand piece's head by virtue of a smaller cross-sectional canister configuration than in prior art canister turbine devices, which typically have used same-diameter bearings and have provided a simpler, and larger, cylindrical canister. Miniaturizing a dental appliance's head naturally gives the dentist or hygienist a better view of the intra-oral work region, as well as rendering the hand piece overall smaller and lighter and more comfortable.

Another inventive feature of the illustrated dental appliance is its ergonomic design, which we believed to be unique. Quite apart from the fact that the use of a molded polymer renders the dental appliance in a look and feel that is quite distinct—and perhaps more attractive and less threatening to the patient than the conventional robotic look and feel of knurled, knobby and shiny stainless steel appliances—the invented case also is shaped with smooth complex curves in orthogonal planes, rather than regimented angles in one plane and a linear taper in the other.

While it will be appreciated that any suitably sized hand piece may be made in accordance with the preferred embodiment of the invention and the preferred process for its manufacture, within the spirit and scope of the invention, the most preferred ergonomic embodiment has an overall length of only approximately 4.45 inches, a diameter tapering from approximately 0.75" down to approximately 0.45" and a weight of only approximately 2 ounces (oz.), less than half that of conventional stainless steel appliances. It will be appreciated that, with an increase in outer diameter of the appliance in the handle region thereof, the interior conduits may be increased in number and/or cross-sectional area. It will also be appreciated that the hand piece may be contoured or textured differently or sized differently for right- or left-handed operation by persons with larger or smaller hands, although it is believed that the hand piece in its described and illustrated form is optimally suited by its symmetry, size and weight for comfortable, fatigue-free operation by anyone.

One important feature of the design of invented appliance 10 is reduction of the size of the head piece. It may be seen that a head piece, indicated generally at 28, and a handle, indicated generally at 30, integrally make up what is referred to herein as hand piece 12. Reduction of head piece 28 is achieved in accordance with the preferred embodiment of the invention by effectively under-sizing the sleeve bearings that mount turbine 18 for rotation within the shape-conforming canister that seals it. It may be seen best by reference to FIGS. 2 and 4 that generally cylindrical head piece 28 is reduced in diameter on either end by using smaller diameter roller bearing assemblies to mount turbine 18 for rotation.

This is an important departure from prior art turbine head design in which the head of the hand piece conforms to a cylindrical turbine, resulting in a comparably greater external diameter on either end of the head including the proximal end including the push button for bur removal and the distal end including the bur. By selecting a smaller diameter bearing subsystem or assembly than the diameter of the turbine, and by conforming the canister walls and the outer 'skin' of the hand piece to the overall profile of the turbine drive assembly including the larger diameter of the centrally located impeller (and its associated spindle) and the smaller diameter of the bearings on either end thereof, a smaller head piece is produced that increases the maneuverability of the head piece within the patient's mouth and the visibility of the patient's mouth therearound and therebehind. It will be understood from FIG. 4 that the roller bearings, spindle and impeller of canister turbine assembly 18 are conventional, but uniquely in accordance with the invention are housed within a shape-conforming, reduced-size canister, as illustrated. Thus, the high speed rotating components of appliance 10 are, for the most part, contained within a volume separate from the interior surfaces of head piece 28.

Those of skill in the art will appreciate that preferably provided also within hand piece 12 is a so-called 'chip air' system for delivering an air and water mixture under pressure to the intra-oral dental drilling site. This is provided in accordance with the preferred embodiment of the invention in the form of two additional smooth, elongate conduits or tubes 32, 34 extending through the interior of hand piece 12 as shown in FIGS. 1 and 3A through 3C. Each conduit has adjacent a proximal end of appliance 10 a couple such as a couple (not shown in FIG. 1, but shown in dashed outline in FIG. 3A) that is plug-compatible, and thus matable for providing an operative connection, with industry-standard sources of pressurized water and air and have adjacent a distal end of appliance 10 one or more outlets directing a coherent stream of the air-water mixture toward the dental drilling site, i.e. toward a point at the distal end of bur 22 where the material removal work is performed.

A feature of the invention in one of its alternative embodiments is the provision of a light source for illuminating the intra-oral region where material is to be removed. Such may be done conventionally, as by the provision within a void provided therefor in hand piece 12 of a light valve preferably in the form of a fiber optic strand or bundle, with a standard light source connection in the proximal end of the appliance. It will be appreciated that, although illustrated in the form of an optic bundle, the light valve may take the form of an integral conduit formed within hand piece 12 during the molding process, with suitable optical surface polishing, coating or other preparation thereof to achieve the internal light reflectivity and conveyance along the extent of hand piece 12.

Those of skill in the arts will appreciate that the chip-air conduits and/or the light valve may be formed or made to extend within the interior of the hand piece by any suitable technique, within the spirit and scope of the invention. For example, the conduits may be formed integrally during the same molding process as is used in accordance with the invention to form the pressurized and exhaust fluid conduits that drive the rotary turbine. It will be appreciated that presently there are limitations on the minimum diameter of such a conduit formed by certain lost-material injection molding techniques. Thus, as the number of conduits to be formed within the interior of the hand piece increases, the process limitation effectively may force an undesirable increase in the diameter of the hand piece. Nevertheless, it is possible to form at least two such conduits for the important turbine drive function and perhaps to form others, depending upon desirable tradeoffs. In accordance with the preferred embodiment of the invention, such chip-air conduits and light valve are made to extend as tubes through one or more of the pressurized and exhaust turbine drive conduits that are integrally formed within the interior of hand piece 12, as described and illustrated herein.

An important feature of the invention may be seen to include the way in which the head of hand piece 12 is formed slightly oversized in one area around the canister turbine. This may best be seen in FIGS. 2 and 5B. It may be seen there that, in a predefined arc around the circular cross section of the cylindrical turbine void, a graduated-diameter venturi structure 40 adjacent the inlet of canister turbine 18. Venturi structure 40 molded into head piece 28, when canister turbine 18 is assembled therein, forms a venturi chamber indicated at 42 that necks down in cross-sectional area, in accordance with a predefined taper, from the distal end of pressurized conduit 14 to the inlet of turbine 18, thereby to accelerate pressurized air immediately before it encounters the turbine's impeller.

It will be appreciated that head piece 28 is formed also from the preferred lost-material casting process, and is molded integrally with handle 30, but utilizes a separate lost-material, e.g. fusible metal, plug that is configured to produce the venturi structure described above and illustrated in FIGS. 2, 5A and 5B in the form of what may be referred to as a 'blister' intentionally formed on the lost-metal core or plug.

Figure 5A:
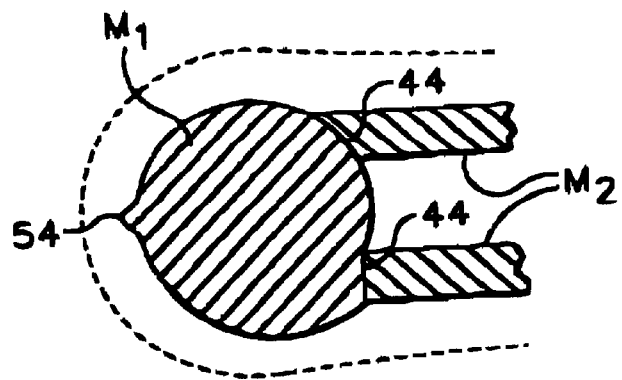
FIGS. 5A and 5B represent a fragmentary top plan view taken generally along the lines 5—5 of FIG. 2 but showing a cavity mold and mold probe configuration in aid of understanding the preferred process of manufacturing the invented appliance.
Figure 5B:
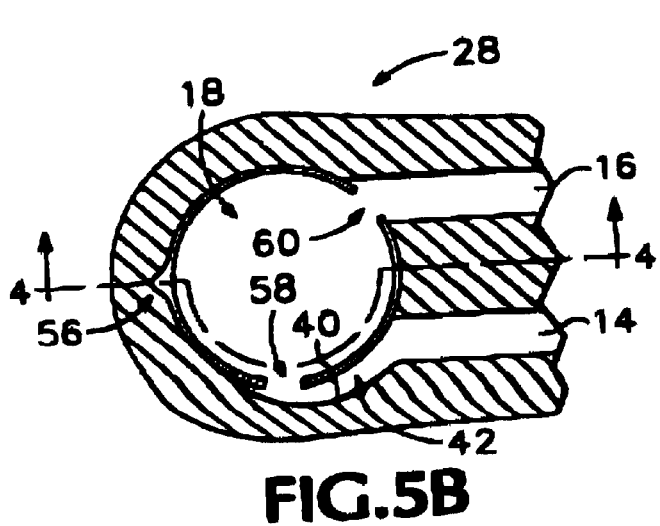

Referring specifically now to FIGS. 5A and 5B, the interface indicated at 44 between the casting probes extending form opposite ends of hand piece 12 is of sufficiently large cross section to render the overall process capable of producing a venturi inlet to turbine 18 that is of less cross-sectional area than otherwise might be possible. In other words, probing with fusible metal interior mold plugs from either end of hand piece 12, siting interface 44 therebetween (by design of the fusible metal probes) relative to the canister turbine assembled within one such void produced by removing the fusible metal interior makes it possible to produce at the interface between one of the voids and the turbine's inlet a region having a cross section of lesser area than that of the cross section of either of the voids. This unique structure makes it possible to form a venturi chamber at the inlet to the turbine's impeller, thereby greatly increasing the velocity of the fluid and the torque of the rotary drive mechanism.

Referring briefly to FIG. 4, another important feature of the invention will now be understood to involve the way a push-button 46 preferably is provided for ejection of a bur from the head of dental appliance 10. First, it will be appreciated that, due to manufacturing tolerances, canister turbine 18 may not be press-fittable into recess 48 thereby to sealingly and securely capture it within head piece 28. Accordingly, in accordance with the preferred embodiment of the invention, two additional measures are taken. It may be seen from FIG. 1 that preferably rubber or plastic O-ring seals 50, 52 are provided that fit around either side of the impeller on the turbine's spindle, which seals seat tightly against the interior or recess 48, as shown. These effectively seal the canister turbine and resists movement along its long axis. Preferably, turbine 18 is further immobilized within recess 48 by a cooperative, elongate keying structure such as an elongate recess 54 formed by molding within recess 48 and a mating elongate ridge 56 formed on an exterior surface of the turbine's canister, as shown. To be discussed immediately below is an end cap that further secures canister turbine 18 within recess 48 and completes the one-time assembly of appliance 10 into a multi-use, auto-clavable, disposable unit.

FIGS. 1 and 4 show push-button 46 to be formed as a part of an end cap that effectively seals the generally cylindrical void into which turbine 18 is fit during assembly of dental appliance 10 and which effectively captures turbine 18 within a recess 48 molded preferably by a lost-material process into head piece 28. Push-button 46 may be provided in any suitable form that is comfortable and convenient to operate by, for example, the user's thumb to eject bur 22. It may be snap-fit into place on the proximal end of head piece 28 as is shown in FIG. 4, it may ultrasonically welded in place or it may be otherwise suitably affixed, all within the spirit and scope of the invention. This is an important feature of the invention: Dental appliance 10 is meant to be disposed of—rather than sent out for maintenance or repair, or disassembled for replacement of the turbine, or refurbished—and its unique construction is consistent with disposal. Thus, push-button 46 and/or another suitable end cap of which push-button 46 may form a part need not be removable even with substantial effort. Instead, entire, integral appliance 10 may be used, autoclaved and reused several times and then cost-effectively discarded or recycled and replaced.

Push-button 46 may be formed as illustrated in FIG. 2, in accordance with a recommended embodiment of the invention, integral with the end cap for head piece 28, as a formed leaf spring having a once-installed-permanently-captured, formed annulus that snap fits within a molded annular recess formed within head piece 28. This configuration provides a number of advantages over conventional push-buttons. Push-button 46 may be seen preferably to be formed a generally circular disk of approximately the same diameter as the proximal diameter of head piece 28 on which it is mounted. Push-button 46 preferably extends inwardly from an annular shoulder region that is dimensioned to be captured by any suitable means, preferably by a snap-fit annular mating structure molded into head piece 28 and formed in push-button 46 as shown in fragmentary detail in FIG. 4.

It may be seen from FIG. 4 that a separate end cap 47 may be provided in conjunction with push-button 46 to capture canister turbine assembly 18 within recess 48, but those of skill in the arts will appreciate that push-button 46 and end cap 47 may be formed integrally, or in any suitable configuration that is consistent with the unitary, durable, auto-clavable and disposable nature of invented appliance 10, within the spirit and scope of the invention. Push-button 46 may be understood to be flexible and to act as a leaf spring with a spring force that normally urges its center outwardly, away from head piece 28, thus obviating other component parts within a push-button assembly as are conventionally required, e.g. one or more coil springs, etc.

It may be seen from FIGS. 1 and 4 that a push rod 49 extends through the center of canister turbine 18 from the proximal end near push-button 46 to the distal end near bur 22. By momentary depression of the center of push-button 46 toward head piece 28, push rod 49 is urged distally along the elongate axis of head piece 28 to force the ejection of bur 22 when it is desired to replace the bur. Once bur 22 is ejected, and another bur installed in head piece 28, push rod 49 is returned to its nominal position immediately adjacent push-button 46 for later bur removal and replacement. It will be appreciated by those skilled in the arts that push-button 46 may be formed to produce so-called snap action (by having formed therein as part of its 'memory' preferential rest and actuated positions of its central region, the former being the nominal position to which the push-button automatically returns when it is released), as is known for example in the membrane keypad field, such that it provides audio and/or tactile feedback to the user of appliance 10.

The invented process for manufacturing invented appliance 10 now may be understood by those of skill in the arts. Preferably, appliance 10 is injection molded as a unitary piece having elongate conduits or voids formed therein during the molding process via lost-material, e.g. lost-metal, casting. By manufacturing at least the case or hand piece 12 in this manner, the prior art problems involving seams and adhesives are avoided in the critical high-pressure-withstand regions of the hand piece's interior. As a beneficial result, the unitary molded hand piece that results from the invented method of manufacture is durable and reliable in the difficult intra-oral environment in which high-pressure fluid flow and high-speed drilling stresses the hand piece in various potentially destructive ways.

Autoclaving of dental appliances between uses is critically important to the hygiene and safety of patients, dentists and hygienists alike. Prior art approaches to lowering cost of dental appliances have attempted to avoid the autoclaving requirement by making multi-part, plastic, intra-oral instruments that are disposable after a single use, as discussed above. Unfortunately, such appliances, for the most part, are unreliable, having not survived the rigors of speed and vibration demanded of high-speed drilling. Importantly, the material composition and integral structure of invented dental appliance 10 described and illustrated herein uniquely meet the tough durability and reliability requirements of the dental practice for multiple use, with autoclaving between uses.

Materials have been found that are sufficiently strong and durable to be manipulated; sufficiently elastic to be comfortable; and sufficiently high-temperature-withstand, dimensionally stable and strong to be auto-clavable. They include a liquid crystal polymer (LCP) marketed under the brand name Vectra™, as well as polycarbonate, polysulfone, polyphenylene sulfide and polyetherimide. Similarly, the lost-material integral molding process described and illustrated herein has been found to be suitably repeatable to produce mass quantities of high-quality plastic hand pieces at reasonably low cost. Nevertheless, other polymeric and alternative, suitably moldable but high-temperature-withstand, relatively inexpensive materials, e.g. metals, and molding processes, e.g. lost-wax investment casting, are contemplated, and are believed to be within the spirit and scope of the invention.

It is desired that—in order to avoid prior art problems in plastic dental hand pieces including slow or fast hydraulic pressure loss characterized by leakage or blow-out—dental appliances be able to withstand the relatively high hydraulic stresses that characterize repeated, cyclic use of the appliance. Normal hydraulic pressures of operation of a high-speed dental drill are 35 pounds per square inch (psi). Accordingly, the invented dental hand piece preferably is specified and tested repeatedly to be able to withstand pressures greater than this nominal requirement, e.g. approximately 52.5 psi (150% of normal), or even of approximately twice this nominal operating pressure, i.e. approximately 70 psi. Again, the unique material and structural configuration of invented dental appliance, as well as the preferred method for its manufacture, have been found to meet or exceed such specifications.

The preferred process for manufacture of the invented apparatus now may be understood to include 1) providing a cavity mold having an elongate, angled central void; 2) extending a mold probe of fusible material into either end of the cavity mold, one such mold probe including two elongate fingers and the other such mold probe including a generally cylindrical mass, said extending being performed in such manner that a tip of one of such elongate fingers contacts a side of such cylindrical mass in a predefined location, preferably adjacent a 'blister' or distended side of the otherwise generally circularly cross-sectioned cylindrical mass; 3) injecting a casting compound, e.g. a polymer, into the recesses formed between the fingers, the barrel and the cavity mold; 4) curing the casting compound within the recesses; and 5) heating the first and second probes to liquify the fusible material of which they are formed, thereby voiding interior regions within the cured casting compound to produce interconnected conduits extending from one end of the cured casting compound to the other.

Preferably, of course, the curing step involves heating the mold containing the mold probes and the cast polymer within the recesses thereof to a temperature that, while substantially higher than the melting point of the fusible material nevertheless is substantially less than the melting point of the cast polymer. This is preferably performed in accordance with the process described above as one similar to the CoreTech™ process that is well known and will not be described or illustrated further herein. In this manner, then, it will be appreciated that the two or more conduits such as conduits 14, 16 may be formed along the axial extent of handle 30 of hand piece 12 and the recess for the canister turbine may be formed in head piece 28 of hand piece 12.

Importantly, the conduits will intersect, or open into, the turbine recess in an inlet and outlet region of the centrally located impeller of the turbine, with pressurized conduit 14 opening adjacent the 'blister' region that becomes venturi chamber 42 when canister turbine 18 is fitted into the recess. Conduits 14, 16 will be smooth and roundly angled through the bend through which hand piece 12 extends, and without further processing are capable of handling the pressure and flow of fluid therethrough for the fluid drive of the rotary turbine drive mechanism. Moreover, the transition from conduit 14 into recess 48 will be smooth and relatively free of burrs for the smoothly controlled flow of fluid under pressure, e.g. air, from the pressurized drive inlet in the proximal end of appliance 10, through venturi chamber 42, through turbine 18, and back out the exhaust outlet in the proximal end of appliance 10.

Referring now briefly to FIGS. 5A and 5B, it may be seen how the above-described cavity mold and plug molds cooperate with one another in a transition region between handle 30 and head piece 28, shown in cross-sectional, fragmentary detail, to form a venturi chamber adjacent the inlet to the turbine. FIG. 5A shows a generally cylindrical mass $M_1$ representing recess 48 in a simplified cross-sectional, fragmentary view within a dashed outline that represents the interior surface contour of the cavity mold. FIG. 5A also shows the tips of elongate finger-shaped masses $M_2$ representing conduits 14, 16. It is noted that the two masses $M_1$ and $M_2$ are the formed mold probes that, in accordance with the preferred process of manufacture of the invented device, are in place during the injection molding of the polymeric casting therearound within the recesses formed between the mold probes and the mold cavity and, after setting or curing of the casting compound, these masses are liquefied to remove them, leaving an interior void within hand piece 12 that becomes recess 48 and conduits 14, 16.

The interfaces between the two different masses are configured, as shown, to be in abutting contact at the tips of the fingers. By forming cylindrical mass $M_1$ with the illustrated 'blister' at approximately 4 to 8 O'clock to form what is referred to herein as venturi structure 40 in the finished molded head piece 28 of hand piece 12, it will be appreciated that the finger mold probe representing pressurized conduit 14 requires no taper down to a cross-sectional dimension that is smaller than advisable using the described lost-material process. A venturi chamber 42 as is described above nevertheless may be provided in accordance with the invented dental appliance 10 in its preferred embodiment.

As may be seen in FIG. 5B, the result of liquifying and removing the probe masses $M_1$ and $M_2$ after injection molding with polymeric casting compound (shown in FIG. 5B in cross section), coupled with the fitting of canister turbine assembly 18 greatly simplified in FIG. 5B by showing only the canister, or skin, enclosure therearound) within recess 48, produces a smoothly tapered cross-sectional area venturi chamber 42 between conduit 14 and turbine inlet 58. It will be understood that the venturi chamber accelerates the pressurized fluid flowing in conduit 14 toward the turbine's impeller (not shown in FIG. 5B), thereby to urge high-speed and thus high-torque clockwise rotation of the turbine and exit of the fluid through turbine outlet 60 into exhaust conduit 16.

Because appliance 10 is unitary and seamless, there is far greater pressure-withstand capability, temperature-withstand capability, and shock and vibration-withstand capability than with prior art dental appliances made of plastic. As a result, the invented appliance may be manufactured inexpensively enough to be used several times, autoclaved between uses and then disposed of or recycled, without the cost that attends refurbishment or repair. It is plug-compatible with existing drive equipment, as it complies with applicable international standards, and is easily, effectively and comfortably manipulated.

METHOD OF USE OF THE INVENTION

Those of skill in the art will appreciate that the invented apparatus may be used in any suitable dental hygiene or treatment application such as the drilling and cleaning of teeth, although appliance 10 will be understood preferably to be used for high-speed drilling operations wherein decadent dental material must be removed. The dental professional typically would hold appliance 10 in the hand and insert the head piece and part of the handle into the patient's mouth, where by virtue of its tiny head size and comfortable grip, maneuverability, visibility and accuracy in decayed material removal is made possible by the invention. Of course, the rotational speed of the turbine within the head piece of appliance 10 is conventionally controlled by air pressure fed thereto via power source 26, with the speed being controlled by any suitable means, e.g. depression of a foot pedal connected thereto.

Importantly, appliance 10 may be autoclaved between patients to ensure each patient's hygiene and safety. This is made possible due to the choice of materials from which case 12 preferably is made and due to the process by which preferably the materials are injection molded, as described and illustrated. Moreover, appliance 10 may be disposed of, turbine and all, after several uses. This benefit is made possible also by the structural configuration, choice of materials and method of manufacture of appliance 10 whereby the cost of manufacture and thus the replacement cost is extremely low relative to that of conventional dental appliances. Nevertheless, appliance 10 is of extremely high quality, and the elasticity and durability resulting from its material and manufacturing process yield enduring, high-speed, reliable performance and patient and dentist safety and comfort.

It will also be appreciated that bur removal may be easily accomplished via the provided push-button on the head piece of appliance 10, and that conventional control of chip-air and, optionally, of a light source is possible, as described and illustrated herein. The material and molding processes described herein will be understood to be applicable also to the manufacture of unitary molded dental appliances such as low-speed, prophylactic devices such as cleaners and polishers, as well as other intra-oral devices such as intra-oral charge-coupled device (CCD) camera or other visual imaging devices. All such natural extensions of the teachings of the present application are contemplated, and are within the spirit and scope of the invention.

Accordingly, while the present invention has been shown and described with reference to the foregoing preferred device and method for its use, it will be apparent to those skilled in the art that other changes in form and detail may be made therein without departing from the spirit and scope of the invention as defined in the appended claims.

We claim:

1. A dental appliance comprising:
    an integrally molded elongate hand piece having an external couple adjacent a proximal end thereof and a rotary drive mechanism adjacent a distal end thereof, and
    one or more fluid drive medium conduits formed within the interior of said hand piece, said conduits extending axially therethrough to communicate fluid under pressure from said proximal end to said rotary drive mechanism, wherein at least one of said fluid drive medium conduits formed therein is characterized by a smooth complex curvature along a substantial portion of the length of said hand piece, said at least one fluid drive medium conduit being integrally and concurrently molded with said hand piece by a lost-material casting process.

2. The appliance of claim 1, wherein said rotary drive mechanism includes a canister-type turbine in fluid communication with at least one of said one or more conduits.

3. The appliance of claim 2, wherein said hand piece includes an elongate handle region and a head region integrally molded by a singular casting process, said head region housing said turbine.

4. The appliance of claim 3, wherein said head region has formed therein a venturi providing a fluid connection between one of said conduits and said turbine.

5. The appliance of claim 3 in which said turbine includes a rotatable impeller, wherein said fluid medium conduits are two in number and wherein said conduits are in fluid communication with one another through said turbine when said impeller is rotating.

6. The appliance of claim 3, wherein said hand piece with said turbine housed in said head region is capable of withstanding fluid pressures of up to approximately seventy pounds per square inch.

7. The appliance of claim 3, wherein said hand piece with said turbine housed in said head region is capable of withstanding fluid pressures of up to approximately fifty pounds per square inch.

8. The appliance of claim 3, wherein said hand piece with said turbine housed in said head region is capable of withstanding fluid pressures of up to a normal operating pressure of approximately thirty-five pounds per square inch.

9. The appliance of claim 1, wherein said hand piece is integrally molded by a lost-material casting process.

10. The appliance of claim 9, wherein said lost-material includes fusible metal.

11. The appliance of claim 1, wherein said hand piece is formed of a material chosen from a group including liquid crystal polymer, polycarbonate, polysulfone, polyphenylene sulfide and polyetherimide.

12. A dental appliance for mounting a tool within a chuck on a distal end thereof, the dental appliance comprising:
    an elongate hand piece having an external couple adjacent a proximal end thereof and a rotary drive mechanism adjacent a distal end thereof in a head region of said hand piece, wherein said head region includes a push rod extending from a distal end of the head region to the proximal end of the head region and a push-button in the proximal end of the head region, the push-button being operatively coupled with the chuck for ejecting the tool, and
    one or more fluid drive medium conduits formed therein during the molding of said hand piece, said conduits extending axially therethrough to communicate fluid under pressure from said proximal end to said rotary drive mechanism.

13. The appliance of claim 12, wherein said push-button includes a leaf spring an exposed outer surface of which is depressed to eject the tool.

14. In a hand-operable dental appliance including a hand piece mounting a rotary drill and further including a fluid pressure source for powering the drill, the improvement comprising:
    rendering the hand piece in unitary form to include an elongate handle region and a head region, the head region having formed therein a venturi structure that cooperates with a canister turbine drive assembly to form a smooth transitional tapered void within said head region between a fluid pressurizable conduit within such elongate handle region and an inlet of such turbine drive assembly.

15. The improvement of claim 14, wherein said venturi structure is formed by a lost-material casting method whereby a peripheral wall of said venturi structure is formed by inserting into a cavity mold for casting such head region a generally cylindrical mass of fusible material having a distended generally cylindrical periphery that is dimensioned to form a semi-circular gap around the circular periphery of such turbine assembly near such inlet of such turbine assembly.

16. In a hand-operable dental appliance including a hand piece mounting a rotary tool and further including a fluid pressure source for powering the tool, the improvement comprising:
    a unitary seamless body including an elongate handle portion and a generally barrel-shaped head portion extending transverse to said handle portion, said head portion having a cavity extending thereinto from one end of said head portion, said cavity having a generally circular cross section for receiving a rotary turbine assembly therein;
    one or more fluid communication conduits extending within said elongate handle portion of the body for fluid communication between a fluid pressure source and said cavity, said conduits being formed as interior elongate voids within said body wherein said interior surfaces of said body define outer surfaces of said conduits; and a rotary turbine assembly within said cavity, said turbine assembly including a rotatable spindle having a long axis, said spindle mounting an impeller for rotation of the latter when fluid under pressure is applied to one of said conduits with said other of said conduits exhausting said fluid under pressure, said turbine assembly further including a bearing assembly and an outer sleeve substantially enclosing said spindle, said impeller and said bearing assembly, with said bearing assembly fixedly mounted within said sleeve for rotation of said spindle mounting said impeller relative to said bearing assembly and said sleeve.

17. The improvement of claim 16, wherein said bearing assembly includes two bearings each of which is positioned on either end of said impeller and surrounding said spindle, wherein said impeller is dimensioned with a first diameter and wherein said bearings are dimensioned with a second diameter smaller than said first diameter and wherein said sleeve substantially conforms to a cross-sectional profile of said spindle, said impeller and said bearings taken in a plane including the spindle's long axis.

18. In a hand-operable dental appliance including a hand piece mounting a rotary tool and further including a fluid pressure source for rotating the tool, the improvement comprising:

an enclosure for a turbine drive mechanism operatively coupled with the rotary tool for rotation of the same, said enclosure including a generally cylindrical recess for housing the turbine drive mechanism, said recess providing a generally circular opening in said enclosure, said enclosure further including a push rod extending axially through said recess between the rotary tool and said opening, and an end cap mounted on said enclosure to enclose the turbine drive mechanism within said enclosure, said end cap including a push-button for engaging said push rod to eject the tool outwardly away from the hand piece when the push-button is depressed, said push-button being generally circular and resiliently flexible to assume a first nominal position of rest against the push rod and a second temporary ejection position effected by momentary depression thereof of urging the push rod to eject the tool.

19. The improvement of claim 18, wherein said push-button is in the form of a leaf spring characterized by a snap action that provides feedback to a user when said push-button is depressed sufficiently to eject the tool.

20. A method for manufacturing an integrally formed dental handpiece for drilling, shaping, finishing or polishing operations, the method comprising:

providing a cavity mold having an elongate, angled central void;

extending a mold probe of fusible material into either end of the cavity mold, one such mold probe including two elongate fingers and the other such mold probe including a generally cylindrical mass, said extending being performed in such manner that a tip of one of such elongate fingers contacts a side of such cylindrical mass in a predefined location;

injecting a casting compound into the recesses formed between the fingers, the barrel and the cavity mold;

curing the casting compound within the recesses; and heating the first and second probes to liquify the fusible material of which they are formed, thereby voiding interior regions within the cured casting compound to produce interconnected conduits extending from one end of the cured casting compound to the other.

21. The method of claim 20, wherein said extending step is performed in such manner that said predefined location of contact between such tip of one of such elongate fingers and such side of such generally cylindrical mass is adjacent a distended side of the otherwise generally circularly cross-sectioned cylindrical mass.

* * * * *